United States Patent
Suzuki et al.

(10) Patent No.: US 9,170,188 B2
(45) Date of Patent: Oct. 27, 2015

(54) STEREOSCOPIC DISPLAY OF BIOLOGICAL PARTICLE MEASUREMENT DATA

(75) Inventors: Shunsuke Suzuki, Kanagawa (JP); Atsuo Fujimaki, Tokyo (JP); Yoshitsugu Sakai, Kanagawa (JP)

(73) Assignee: Sony Corporation, Tokyo (JP)

( * ) Notice: Subject to any disclaimer, the term of this patent is extended or adjusted under 35 U.S.C. 154(b) by 731 days.

(21) Appl. No.: 13/302,712

(22) Filed: Nov. 22, 2011

(65) Prior Publication Data

US 2012/0139917 A1    Jun. 7, 2012

(30) Foreign Application Priority Data

Dec. 3, 2010   (JP) .................. 2010-269946

(51) Int. Cl.
*G09G 5/00* (2006.01)
*G01N 15/14* (2006.01)
*G06T 19/00* (2011.01)

(52) U.S. Cl.
CPC ........ *G01N 15/1429* (2013.01); *G01N 15/1459* (2013.01); *G01N 15/1463* (2013.01); *G01N 2015/1402* (2013.01); *G01N 2015/1445* (2013.01); *G01N 2015/1493* (2013.01); *G06T 19/00* (2013.01)

(58) Field of Classification Search
None
See application file for complete search history.

(56) References Cited

U.S. PATENT DOCUMENTS

| | | | |
|---|---|---|---|
| 6,195,205 B1 * | 2/2001 | Faris | 359/465 |
| 2010/0110103 A1 * | 5/2010 | Ramirez et al. | 345/619 |
| 2010/0149174 A1 * | 6/2010 | Nakao et al. | 345/419 |

FOREIGN PATENT DOCUMENTS

JP    2006-017497    1/2006

OTHER PUBLICATIONS

Leauhatong et al.; "Data Scattering Algorithm for Very Large Multivariable Data Visualization;" The 1998 IEEE Asia-Pacific Conference on Circuits and Systems, Nov. 1998; pp. 591-594; IEEE.*
Daniel B. Carr; "Multivariate Graphics;" Encyclopedia of Biostatistics in 2005 by John Wiley & Sons, Ltd.; Published Online: Jul. 15, 2005; DOI: 10.1002/0470011815.b2a13051.*

* cited by examiner

*Primary Examiner* — Edward Martello
(74) *Attorney, Agent, or Firm* — Sony Corporation (57) ABSTRACT

A 3D data analysis apparatus includes a data storage unit configured to store measurement data of microparticles, an input unit configured to select four independent variables from the measurement data, a data processing unit configured to calculate a position in a coordinate space using three variables of the selected variables as coordinate axes, calculate a figure from one residual variable of the selected variables, and create a 3D stereoscopic image showing a characteristic distribution of the microparticles, and a display unit configured to display the 3D stereoscopic image.

17 Claims, 9 Drawing Sheets

STEREOSCOPIC DISPLAY OF BIOLOGICAL PARTICLE MEASUREMENT DATA

CROSS REFERENCES TO RELATED APPLICATIONS

The present application claims priority to Japanese Patent Application No. 2010-269946 filed on Dec. 3, 2010, the disclosure of which is incorporated herein by reference.

BACKGROUND

The present disclosure relates to a 3D data analysis apparatus, a 3D data analysis method and a 3D data analysis program, and, more particularly, to a 3D data analysis apparatus for displaying measurement data of microparticles by a 3D stereoscopic image, and the like.

In order to analyze microparticles such as bio-related particles such as cells, microorganisms and liposomes or synthetic particles such as latex particles, gel particles and industrial particles, a microparticle measurement device of introducing dispersed liquid of microparticles into a channel and measuring optically, electrically or magnetically microparticles has been used.

As an example, there is a particle analyzer for discriminating synthetic particles according to the size or shape thereof. As parameters which may be measured by the particle analyzer, there are an elementary composition and a particle diameter of a microparticle and the like.

A flow cytometer (flow cytometry) is used to analyze bio-related particles. As parameters which may be measured by the flow cytometer, there are forward scattered light (FS), side scattered light (SS), fluorescence (FL), impedance and the like of the microparticles. Forward scattered light (FS), side scattered light (SS) and fluorescence (FL) are used as parameters showing optical characteristics of cells or microorganism (hereinafter, merely referred to as "cells") and impedance is used as a parameter showing the electrical characteristics of cells.

More specifically, first, forward scattered light is light which is scattered at a small angle in a front direction with respect to a laser light axis and includes scattered light, diffracted light and refracted light of laser light generated at surfaces of cells. Forward scattered light is mainly used as a parameter showing the size of the cells. Next, side scattered light is light scattered at an angle of about 90 degrees with respect to a laser light axis, and is a scattered light of the laser light generated in a granule or nucleus inside the cell. Side scattered light is mainly used as a parameter showing the internal structure of cells. Fluorescence is light generated from a fluorescent pigment which is labeled at the cells and is used as a parameter showing presence/absence of a cell surface antigen recognized by a fluorescent pigment labeled antibody, the amount of nucleic acid coupled with a fluorescent pigment and the like. In addition, impedance is measured by an electrical resistance method and used as a parameter showing the volume of cells.

In order to analyze measurement data in a flow cytometer, a data analysis apparatus for plotting a measurement value of each cell with respect to the axis of such a measurement parameter and creating and displaying a drawing showing a characteristic distribution of cells in a cell group is used. A one-dimensional distribution map using one measurement parameter is also referred to as a histogram and is created as a graph in which an X axis denotes a measurement parameter and a Y axis denotes the number (count) of cells. A two-dimensional distribution map using two measurement parameters is also referred to as a cytogram and is created by plotting cells based on the measurement values thereof in a coordinate plane in which an X axis denotes one measurement parameter and a Y axis denotes the other measurement parameter.

Since unnecessary cells which are not analysis objects are included in a cell group used as a sample, measurement data is analyzed after picking out a cell sub-group, which is an analysis object, from the cell group used as the sample. The cell sub-group, which is the analysis object, is picked out by specifying a region, in which the cell sub-group is present, on the histogram or the cytogram. This operation is called "gating" because target cells are surrounded in the region specified on the histogram or the cytogram.

On the histogram having one measurement parameter as an axis or the cytogram having one combined measurement parameter as an axis, a cell sub-group which is an analysis object and unnecessary cells may be present in an overlap region. For example, when a lymphocyte is analyzed using human peripheral blood as a sample, some monocyte and lymphocyte may be present in the same region on the cytogram having forward scattered light (FS) and side scattered light (SS) as axes. Accordingly, when gating is performed, it is necessary for the user to specify the region in which monocyte is not surrounded and only lymphocyte is present.

In order to specify the region so as to surround only the cell sub-group to be analyzed without surrounding unnecessary cells, in the related art, it is necessary for the user to perform gating with reference to a plurality of histograms or cytograms. The number of measurable parameters has been increased in association with improvement in performance of a flow cytometer. Thus, it is necessary for the user to refer to more histograms or cytograms. At this time, it is necessary for the user to perform a gating operation while recalling a stereoscopic distribution map (3-dimensional distribution map) obtained by two cytograms.

In order to support the gating operation of the user, Japanese Unexamined Patent Application Publication No. 2006-17497 proposes an analysis apparatus including measurement data acquiring means for acquiring first, second and third measurement data from an analyte, three-dimensional distribution map creating means for creating a three-dimensional distribution map showing a distribution of a tangible component included in the analyte using the first, second and third measurement data as the axes, region setting means for setting the fraction region on the three-dimensional distribution map to be changable, and a reference distribution map creating means for creating at least one of a two-dimensional distribution diagram using the first and second measurement data as axes and a frequency distribution map using the first measurement data as the axis with respect to the tangible component belonging to the fraction region set by the region setting means (see claim 9 of Japanese Unexamined Patent Application Publication No. 2006-17497). According to the analyzing apparatus, it is possible to set the fraction region on the three-dimensional distribution map while referring to the two-dimensional distribution map (cytogram) and the frequency distribution map (histogram) displayed along with the three-dimensional distribution map. In addition, the three-dimensional distribution map of this analysis apparatus is planarly displayed on the display and is not stereoscopic.

In association with the present disclosure, a two-eye stereo three-dimensional image technique (3D stereoscopic image technique) will be described. In the two-eye stereo three-dimensional image, first two images are obtained when a right eye and a left eye view of an object are prepared. Such images are simultaneously displayed, a right-eye image is provided only to a right eye and a left-eye image is provided only to a left eye. Thus, an image projected on the eye when viewing an object in a three-dimensional space is reproduced such that the user stereoscopically views the object.

In a 3D display in which a stereoscopic view is enabled, (a) a glasses system, (b) a naked-eye system and (c) a viewer system are mainly employed. In (a) the glasses system, there are an anaglyph system, a polarized filter system and a time division system. In (b) the naked-eye system, there are a parallax barrier system and a lenticular system and, in (c) the viewer system, there are a stereoscope system and a head mount system.

SUMMARY

As described above, in the related art, in the data analysis apparatus used in the flow cytometer, at the time of gating, the user specifies the position of the cell sub-group to be analyzed on the distribution map while referring to a plurality of histograms or cytograms or recalling the stereoscopic distribution map (three-dimensional distribution map) obtained by combining two cytograms.

It is desirable to provide a data analysis apparatus which is capable of easily and intuitively specifying a microparticle and microparticle sub-group to be analyzed on a distribution map without referring to a plurality of histograms or cytograms or recalling a three-dimensional distribution map on the distribution map.

According to an embodiment of the present disclosure, there is provided a 3D data analysis apparatus including: a data storage unit configured to store measurement data of microparticles; an input unit configured to select four independent variables from the measurement data; a data processing unit configured to calculate a position in a coordinate space using three variables of the selected variables as coordinate axes, calculate a figure from one residual variable of the selected variables, and create a 3D stereoscopic image showing a characteristic distribution of the microparticles; and a display unit configured to display the 3D stereoscopic image. According to the 3D data analysis apparatus, it is possible to analyze the measurement data while stereoscopically viewing a three-dimensional distribution map obtained by plotting the microparticles by the figure already, changed according to the measurement value of one parameter in the coordinate space using three parameters as coordinate axes.

According to another embodiment of the present disclosure, there is provided a 3D data analysis method including: selecting four independent variables from measurement data of microparticles; calculating a position in a coordinate space using three variables of the selected variables as coordinate axes; calculating a figure from one residual variable of the selected variables; creating a 3D stereoscopic image showing a characteristic distribution of the microparticles; and displaying the 3D stereoscopic image.

According to still another embodiment of the present disclosure, there is provided a 3D data analysis program for, on a computer, executing: calculating a position in a coordinate space using three variables selected independently from measurement data of a minute particles as coordinate axes; calculating a figure from another independent variable selected from the measurement data of the minute particles; creating a 3D stereoscopic image showing a characteristic distribution of the microparticles; and displaying the 3D stereoscopic image.

In the present disclosure, the "microparticle" widely includes microparticles such as bio-related particles such as cells, microorganisms and liposomes or synthetic particles such as latex particles, gel particles and industrial particles. The cells include animal cells (blood cells, or the like) and plant cells. The microorganisms include bacteria such as colon bacillus, viruses such as tobacco mosaic virus, fungi such as yeasts, or the like. The bio-related particles include chromosomes, liposomes, mitochondria, organelles (cell organelles), or the like, constituting the cells. In addition, the bio-related particles include nucleic acid or protein, or bio-related high molecules such as complex. The industrial particles may be organic or inorganic high-molecular material, metal, or the like. The organic high-molecular material includes polystyrene, styrene divinylbenzene and polymethylmethacrylate, or the like. The inorganic high-molecular material includes glass, silica, a magnetic material, or the like. Metal includes gold colloid, aluminum, or the like. The shape of the microparticle is generally spherical, but may be non-spherical. The size, mass or the like of the microparticle is not specially limited.

According to the present disclosure, it is possible to provide a data analysis apparatus which is capable of easily and intuitively specifying a microparticle and microparticle sub-group to be analyzed on a distribution map without referring to a plurality of histograms or cytograms or recalling a three-dimensional distribution map.

Additional features and advantages are described herein, and will be apparent from the following Detailed Description and the figures.

DETAILED DESCRIPTION

Hereinafter, embodiments of the present disclosure will be described with reference to the drawings. In addition, the following embodiments are examples of the representative embodiments of the present disclosure and the range of the present disclosure is not interpreted narrowly. In addition, the description is given in the following order.

Figure 1:
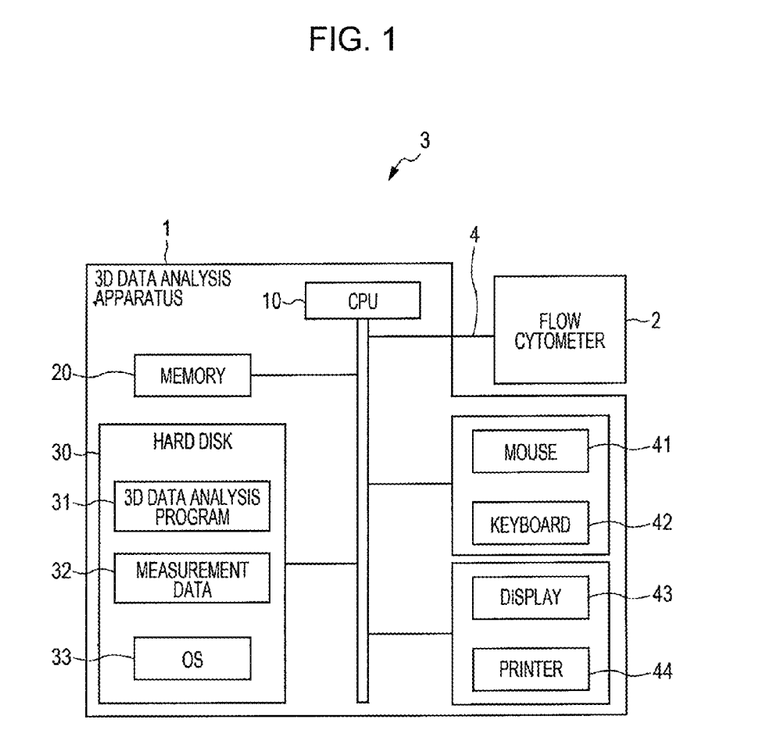
FIG. 1 is a block diagram illustrating the configuration of a 3D data analysis apparatus according to the present disclosure continuously connected with a flow cytometer.
Figure 2:
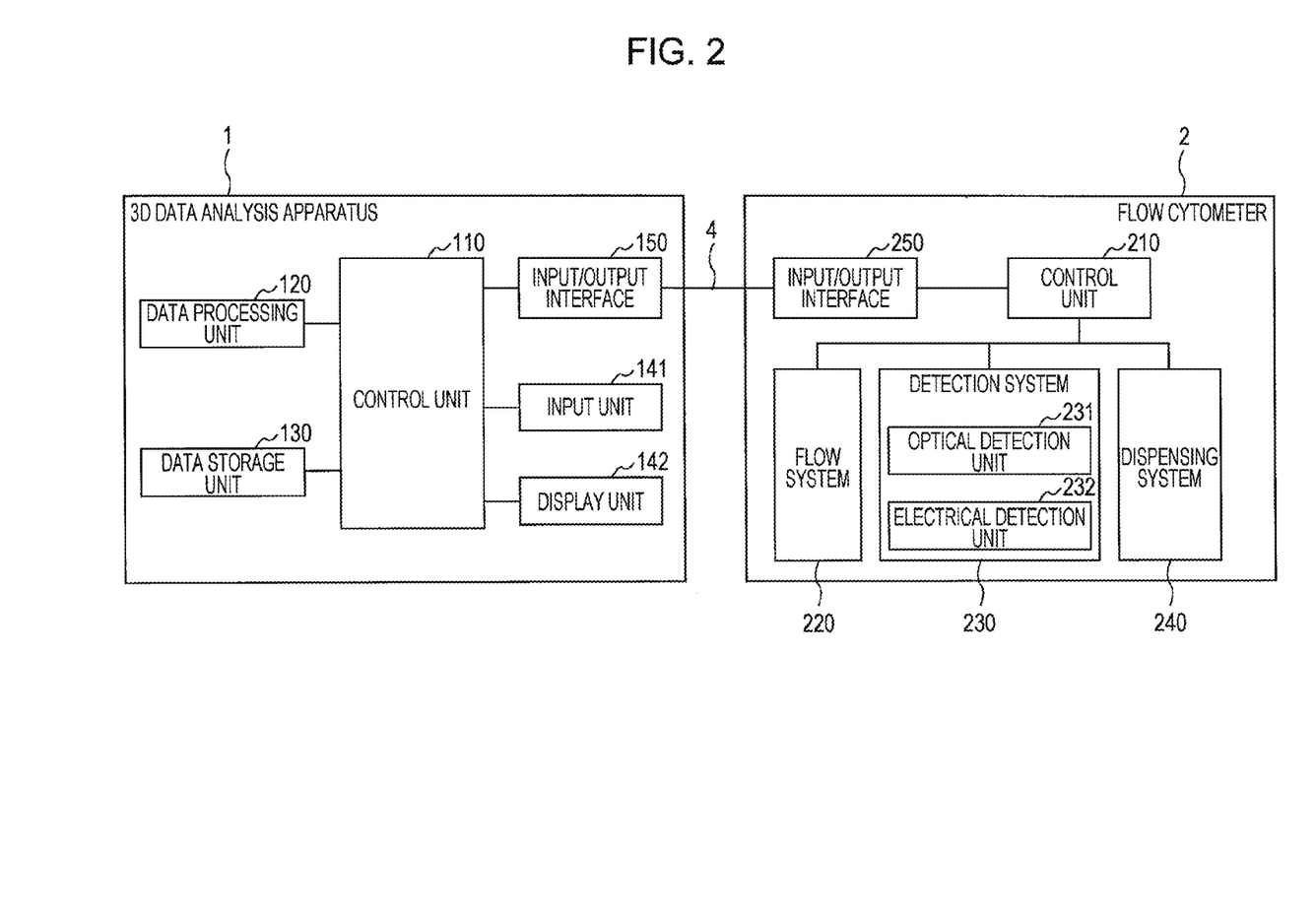
FIG. 2 is a block diagram illustrating the functional configuration of a 3D data analysis apparatus according to the present disclosure.

1. Configuration of 3D Data Analysis apparatus
2. Display of 3D Stereoscopic Image
3. Feature of 3D Stereoscopic Image
   (3-1) Shape of FIG.
   (3-2) Shade Process of FIG.
   (3-3) Coordinate Axis
   (3-4) Moving Image
4. 3D Data Analysis Program 1. Configuration of 3D Data Analysis Apparatus FIG. 1 shows the configuration of a 3D data analysis apparatus according to the present disclosure. Here, an embodiment in which the 3D data analysis apparatus is connected with a microparticle measurement device so as to configure a microparticle analysis system is shown. FIG. 2 shows the functional configuration of the microparticle analysis system. Hereinafter, for example, the case where a flow cytometer is used as a microparticle measurement device will be described.

In the drawings, the 3D data analysis apparatus denoted by reference numeral 1 is connected to the flow cytometer 2 by a communication cable 4 so as to configure the microparticle analysis system 3. The 3D data analysis apparatus 1 includes a central processing unit (CPU) 10, a memory 20, a hard disk 30, a user interface, and the like. A 3D data analysis program 31, microparticle measurement data 32, an operating system (OS) 33, and the like are stored and held in the hard disk 30. A mouse 41 and keyboard 42 for receiving information input by a user, a display 43 and printer 44 for outputting information to the user, and the like are included in the user interface. In addition, instead of or in addition to the mouse 41 and the keyboard 42, a stick controller, a pen tablet, and the like may be provided as an input device.

A data storage device 130 (hard disk 30) stores measurement data 32 of microparticles (cells) output from the flow cytometer 2. The measurement data output from the input/output interface 250 of the flow cytometer 2 is input to the input/output interface 150 of the 3D data analysis apparatus 1 through the communication cable 4 and is stored in the data storage unit 30 (hard disk 30).

The measurement data 32 is processed in a data processing unit 120. The data processing unit 120 begins to receive and process user input from an input unit 141 (the mouse 41, the keyboard 42, and the like). That is, when four variables (parameters) independent of the measurement data 32 are selected and input by the user, the data processing unit 120 creates a 3-dimensional distribution map showing a characteristic distribution of microparticles using three of the selected parameters as coordinate axes. The three-dimensional distribution map is created by plotting microparticles in a coordinate space using the selected three parameters as coordinate axes. The microparticle is plotted by calculating the position of each microparticle in the coordinate space from the measurement values of the selected parameters and drawing a predetermined figure at the calculated position.

In addition, the data processing unit 120 calculates the figure from one residual parameter of the selected parameters. More specifically, the data processing unit 120 calculates the shape, size and/or color of the figure corresponding to each microparticle from the measurement value of this parameter. The figure drawn at the predetermined position in the coordinate space is regarded as a figure having the calculated shape, size and color.

Here, "independent parameters" refer to different parameters selected from forward scattered light (FS), side scattered light (SS), fluorescence (FL), impedance and the like. Fluorescence (FL) may be treated as different parameters for each wavelength band of a fluorescent pigment which has labeled the microparticle and is labeled with FL1, FL2 to FLn (n is an integer of 3 or more). As four independent parameters, for example, there is a combination of forward scattered light (FS), side scattered light (SS), fluorescence (FL1), impedance or a combination of forward scattered light (FS), fluorescence (FL1), fluorescence (FL2) and impedance. In addition, four independent parameters may be arbitrarily selected and combined from measurement data.

The three-dimensional distribution map created by the data processing unit 120 is displayed on the output unit 142 (display 43) as a 3D stereoscopic image. This 3D stereoscopic image is regarded as a two-eye stereo three-dimensional image which will be described in detail later. The display of the 3D stereoscopic image on the output unit 142 may be arbitrarily rotated, enlarged or reduced based on a user input signal from the input unit 141 (mouse 41, keyboard 42, or the like).

The flow cytometer 2 includes the same configuration as the apparatus of the related art or a configuration obtained by appropriately changing the configuration of the apparatus of the related art, and, more specifically, includes a control unit 210, a flow system 220, a detection system 230, and an input/output interface 250, and the like.

The flow system 220 introduces a sample liquid laminar flow including microparticles into the center of a sheath liquid laminar flow in a channel formed in a flow cell or a microchip so as to arrange the microparticles in the laminar flow in a line. The detection system 230 acquires a parameter value representing the characteristics of the microparticles flowing in the channel. More specifically, the optical detection unit 231 irradiates light to the flowing microparticles, detects scattered light, fluorescence or the like generated from the microparticles, and acquires the intensity thereof. The optical detection unit 231 includes a laser light source, a lens, a mirror, a filter, an area imaging device such as a CCD and CMOS device, or a photo multiplier tube (PMT), and the like. The electrical detection unit 232 includes an electrode facing the flowing microparticles and acquires impedance, capacitive value (capacitance), inductance, and the like of the minute particles. The flow cytometer 2 may include a dispensing system for dispensing microparticles which are determined to have desired characteristics as the analysis result. In the dispensing system 240, for example, a system 240 for discharging liquid droplets including microparticles to a space other than a flow cell and controlling movement directions of the liquid droplets so as to collect only desired microparticles in a container may be employed.

The measurement value of the intensity of the scattered light, fluorescence and the like or the measurement value of impedance, capacitive value (capacitance) and inductance and the like detected in the detection system 230 is converted into an electrical signal and is output from the input/output interface 250 as measurement data.

2. Display of 3D Stereoscopic Image

Figure 3:
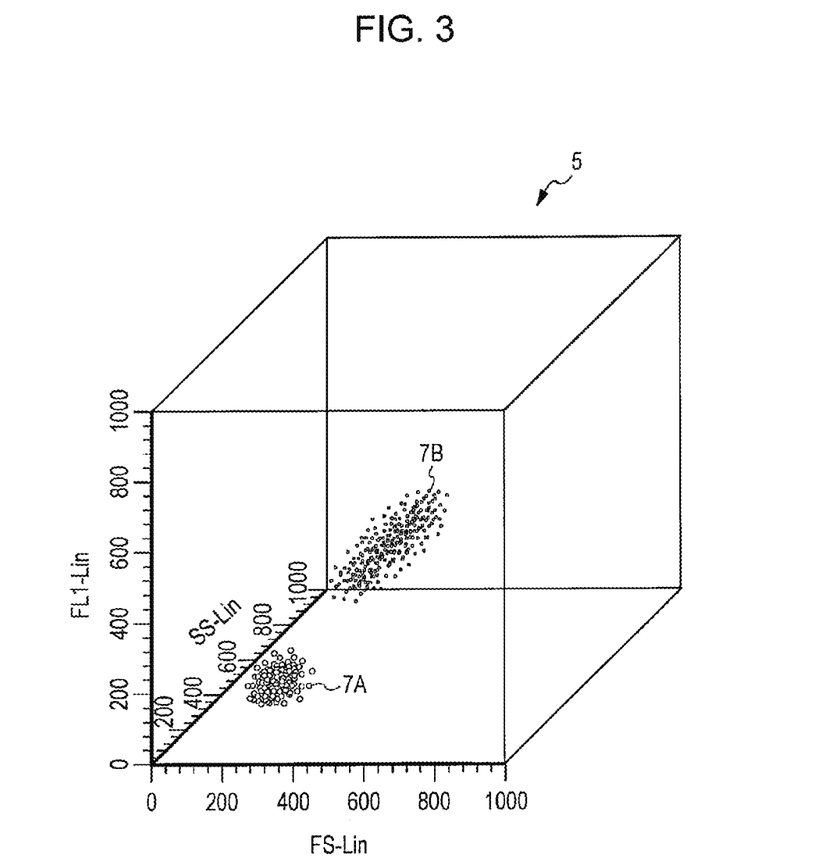
FIG. 3 is a schematic diagram illustrating a three-dimensional distribution map displayed by a 3D data analysis apparatus according to the present disclosure.

FIG. 3 is a schematic diagram illustrating a three-dimensional distribution map displayed by a 3D data analysis apparatus according to the present disclosure. This three-dimensional distribution map may be displayed on the output unit 142 by a 3D stereoscopic image and stereoscopically viewed by the user.

The three-dimensional distribution map 5 shows a characteristic distribution of microparticles in a coordinate space 6 using three parameters selected by the user as coordinate axes. In the three-dimensional distribution map 5, the figure corresponding to each microparticle is drawn at the position calculated from the measurement value of the selected parameters. This figure includes the shape, size or color calculated from the measurement value of one parameter already selected by the user.

In the drawing, in a coordinate space using forward scattered light (FS-Lin: X axis), side scattered light (SS-Lin: Y axis) and first fluorescence (FL1-Lin: Z axis) as coordinate axes, a three-dimensional distribution map in which a figure having a size (volume) calculated from the measurement value of impedance is shown. Impedance is a parameter showing the volume (EV) of the microparticle (particularly, a cell). Reference numerals 7A and 7B denote figures corresponding to two microparticle sub-group having different volumes and denote figures which are calculated as different sizes and drawn because measurement values of impedance are different. The FIG. 7A is drawn such that the size (volume) thereof is greater than that of the FIG. 7B.

In this example, each microparticle is drawn on the distribution map as the figure having the size corresponding to the volume thereof. More specifically, for example, a cell having a large volume is displayed by a larger (large volume) FIG. 7A and a cell having a small volume is displayed by a smaller (small volume) FIG. 7B. Accordingly, according to the three-dimensional distribution map 5, the forward scattered light, side scattered light and first fluorescence of the microparticles and the characteristic distribution of four parameters of the volume may be simultaneously shown.

Although the case where the sizes of the FIG. 7A and the FIG. 7B are calculated from the measurement value of impedance is described as an example, the shape, color (hue, chroma and lightness) of the figure corresponding to the microparticle may be calculated from the measurement value of impedance. For example, the color of the figure may be calculated from the level of the measurement value of impedance. For example, the shape of the figure may be set to another pattern or the color of each figure may be set to another color combination according to the measurement value of impedance. Two or more of the shape, size and color of the figure may be changed.

Although the case where the sizes of the FIG. 7A and the FIG. 7B are calculated from the measurement value of impedance is described as an example, the parameters used to calculate the figure corresponding to the microparticle are not specially limited and, for example, forward scattered light, side scattered light, fluorescence or the like may be used or capacitance, inductance, or the like may be used. For example, if fluorescence is selected, the color of the figure is calculated from the level of the fluorescence intensity. For example, if inductance is selected, the shape of the figure may be set to another pattern according to the measurement value of inductance.

In addition, the parameters of the coordinate axes are not limited to the combination of forward scattered light, side scattered light and first fluorescence and any combination may be used. Forward scattered light, side scattered light, fluorescence or the like may be taken or impedance, capacitance, inductance or the like may be taken on each coordinate axis.

In the three-dimensional distribution map 5, parameters showing the optical characteristics of forward scattered light, side scattered light, fluorescence or the like are used as coordinate axes and the shape, size and/or color of the figure are preferably selected according to the measurement value of impedance, capacitance, inductance or the like. In this case, the data processing unit 120 is configured to calculate the position in the coordinate space from the measurement data of the parameters showing the optical characteristics of the microparticles and calculate the figure from the measurement data of variables showing electrical characteristics.

In particular, the size of the figure is preferably set according to the measurement value of impedance (see FIG. 3). According to the three-dimensional distribution map, it is possible to intuitively confirm the optical characteristic distribution of the microparticles and the volume distribution by the size (volume) of the figure corresponding to each microparticle.

Figure 4:
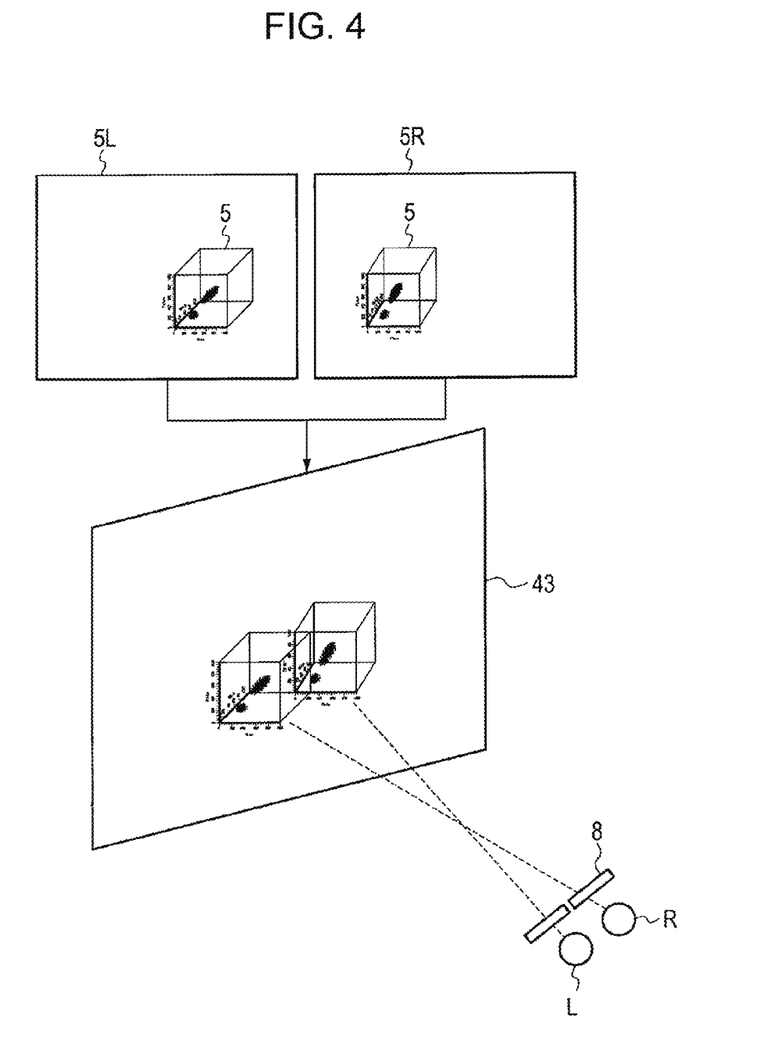
FIG. 4 is a schematic diagram illustrating a two-eye stereo three-dimensional image (3D stereoscopic image) displayed by the 3D data analysis apparatus according to the present disclosure.

The 3D stereoscopic display of the three-dimensional distribution map 5 is performed by a two-eye stereo three-dimensional image. FIG. 4 is a schematic diagram illustrating a two-eye stereo three-dimensional image displayed by the 3D data analysis apparatus according to the present disclosure.

When the user selects parameters, the data processing unit 120 creates the three-dimensional distribution map 5 and creates an image (left-eye image 5L) when viewing the distribution map with the left eye and an image (right-eye image 5R) when viewing the distribution map with the right eye. The output unit 142 (display 43) simultaneously displays the left-eye image 5L and the right-eye image 5R, and separately and respectively provides the left-eye image 5L and the right-eye image 5R to the left eye and the right eye.

Separation provision may be performed by alternately displaying the left-eye image 5L and the right-eye image 5R with a slight time difference and synchronizing shuttered glasses 8 to the images, for example, in a time division system which is one of the glasses system. In separation provision, another glasses system such as an anaglyph system and a polarized filter system, a naked-eye system such as a parallax barrier system and a lenticular system, and a viewer system such as a stereoscope system and a head mount system may be employed.

The display 43 separately provides the left-eye image 5L and the right-eye image 5R such that an image projected on the eye when viewing the three-dimensional distribution map in a three-dimensional space is reproduced. Thus, the user stereoscopically views the distribution map.

In the 3D data analysis apparatus 1, in the coordinate space using three parameters as coordinate axes, the three-dimensional distribution map obtained by plotting microparticles by figures already changed according to the measurement value of one parameter is displayed by the 3D stereoscopic image. Accordingly, the user arbitrarily combines the parameters so as to display the three-dimensional distribution map, thereby obtaining information about four characteristics of the microparticles using one graph. In the 3D data analysis apparatus 1, it is possible to reduce the number of graphs to be referred to so as to perform efficient analysis, as compared to the display using the histograms or cytograms of the related art. The user may analyze measurement data while stereoscopically viewing the three-dimensional distribution map. Accordingly, in the 3D data analysis apparatus 1, it is possible to easily and intuitively specify a microparticle or a microparticle sub-group to be analyzed on the distribution map and it is not necessary to refer to a plurality of histograms or cytograms or recall the three-dimensional distribution map as in the related art.

3. Feature of 3D Stereoscopic Image

Hereinafter, the features of the 3D stereoscopic image displayed by the 3D data analysis apparatus according to the present disclosure will be sequentially described.

(3-1) Shape of Figure

In FIG. 3, the figures corresponding to the microparticles denoted by the reference numerals 7A and 7B are calculated as a polyhedron formed of a combination of polygons having a predetermined shape and are displayed in the 3D stereoscopic image. As described above, the data processing unit 120 calculates the position and figure in the coordinate space of each microparticle based on the measurement value of the parameter selected by the user and creates the three-dimensional distribution map. At this time, the figure is calculated as a polyhedron formed of a combination of polygons having a predetermined shape so as to reduce the calculation load on the data processing unit 120. In addition, the figure is displayed as a polyhedron formed of a combination of polygons having a predetermined shape in the 3D stereoscopic image so as to enhance the 3D effect of the image at the time of stereoscopic viewing.

Figure 5A:
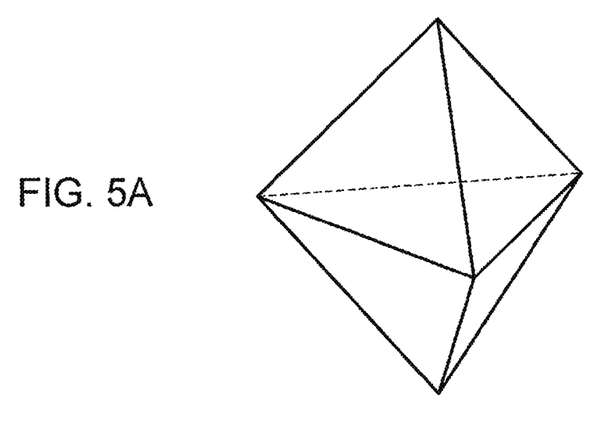
FIGS. 5A and 5B are schematic diagrams illustrating the shape of a figure corresponding to a microparticle in a 3D stereoscopic image.
Figure 5B:
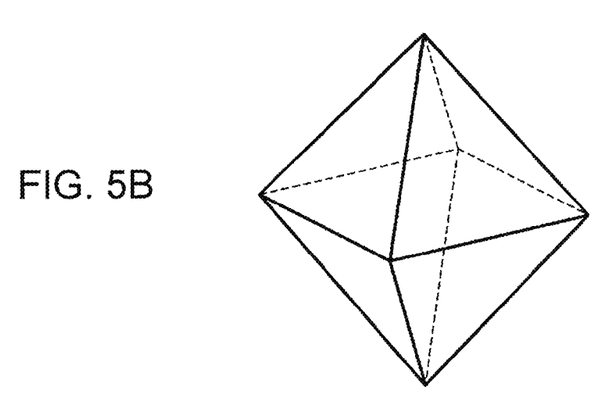

As a polyhedron formed of a combination of polygons having a predetermined shape, for example, a hexahedron formed by combining six triangular polygons shown in FIG. 5A and an octahedron formed by combining eight polygons shown in FIG. 5B may be employed. The shape of the figure may be determined according to the measurement value of the parameter selected by the user and is not specially limited to the polyhedron formed of a combination of polygons having a predetermined shape. However, from the viewpoint of the reduction in calculation load and the 3D effect, a hexahedron or an octahedron is preferable.

(3-2) Shade Process of Figure

In the 3D stereoscopic image, a figure observed at the front side, of the figure corresponding to the microparticle at the time of stereoscopic viewing is heavily displayed and a figure observed at an inner part is lightly displayed. A process of changing the shading of the figure is hereinafter referred to as a "shade process".

Figure 6:
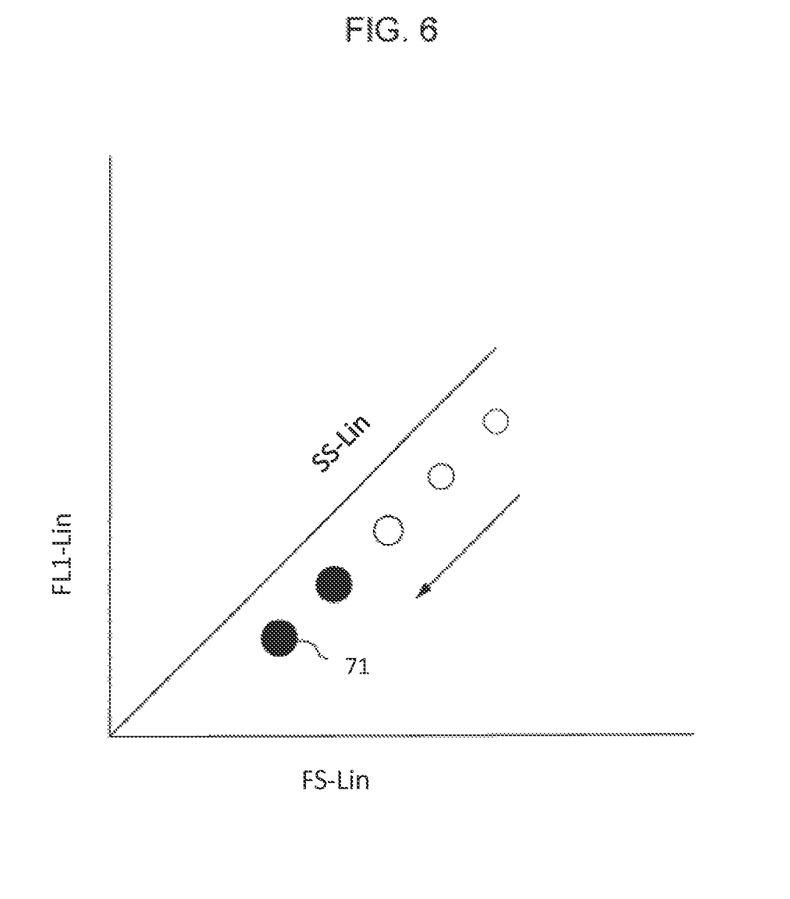
FIG. 6 is a conceptual diagram showing a stereoscopic observation image of a shaded figure.

A conceptual diagram of stereoscopic observation image (hereinafter, simply referred to as a "stereoscopic image") of a figure subjected to the shade process is shown in FIG. 6. FIG. 6 is a conceptual diagram showing a stereoscopic observation image of a shaded figure. In the drawing, a FIG. 7 observed at the front side is heavy and a FIG. 7 observed at an inner part is light according to a direction of an arrow. By performing the shade process of the FIG. 7, it is possible to give a depth to a stereoscopic image of a 3D stereoscopic image so as to improve a 3D effect.

A processing method of a shade process will be described with reference to FIGS. 7A to 7C. The left-eye image and the right-eye image are simultaneously displayed on the display 43 such that the left-eye image and the right-eye image of the FIG. 70 observed at the position of the screen of the display 43 are displayed in an overlapping state at the time of stereoscopic viewing (see FIG. 7B).

In the case where the left-eye image displayed on the display 43 is located on the right side of the right-eye image (see FIG. 7A), the figure is stereoscopically viewed in front of the position of the screen of the display 43. The stereoscopic image of the figure observed outside the screen position is denoted by reference numeral 71 of the drawing, the left-eye image of the FIG. 7A displayed on the display 43 is denoted by reference numeral 71L, and the right-eye image is denoted by reference numeral 71R. In the case where the left-eye image displayed on the display 43 is located on the left side of the right-eye image (see FIG. 7C), the figure is stereoscopically viewed behind the position of the screen of the display 43. The stereoscopic image of the figure observed outside the screen position is denoted by reference numeral 72 of the drawing, the left-eye image of the FIG. 7C displayed on the display 43 is denoted by reference numeral 72L, and the right-eye image is denoted by reference numeral 72R.

Figure 7A:
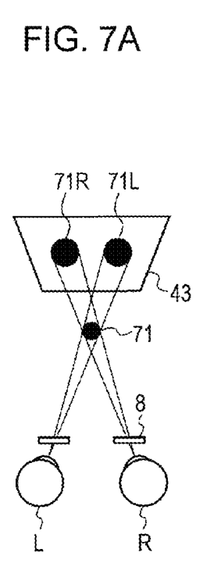
FIGS. 7A to 7C are schematic diagrams illustrating a processing method of a shade process.
Figure 7B:
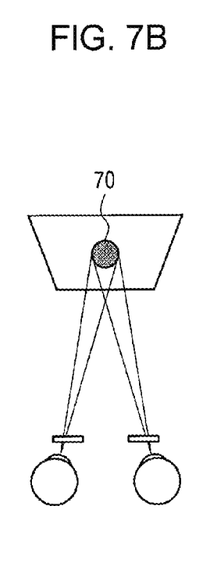
Figure 7C:
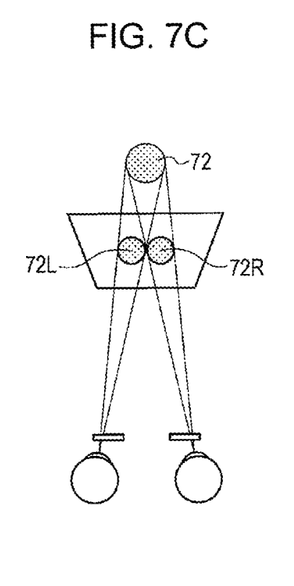

In the shade process, the left-eye image 71L and the right-eye image 71R of the FIG. 7A observed from a front side is heavily displayed and the left-eye image 72L and the right-eye image 72R of the FIG. 70 observed at the inner part is lightly displayed.

(3-3) Coordinate Axis

Figure 8:
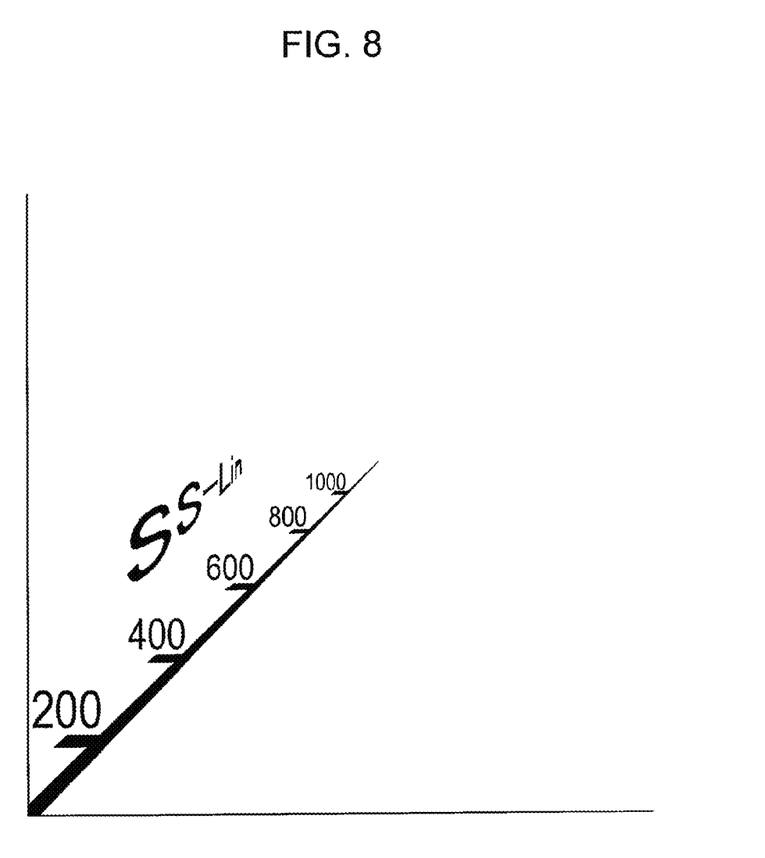
FIG. 8 is a conceptual diagram illustrating a stereoscopic observation image of a coordinate axis.

In the 3D stereoscopic image, only a part observed from a front side of a coordinate axis at the time of stereoscopically viewing is thickly displayed and a part observed at an inner part is thinly displayed. A conceptual diagram of a stereoscopic image of the coordinate axis with a changed thickness is shown in FIG. 8. As such, by changing the thickness of the coordinate, a depth can be applied in the stereoscopic image of the 3D stereoscopic image, thus 3D effect can be improved.

As shown in FIG. 8, when stereoscopically viewing a scale interval of the coordinate axis, a part observed from a front side is widely displayed and a part observed at an inner part is narrowly displayed such that a depth is further given to the stereoscopic image. Characters of a coordinate axis name (SS-Lin in the drawing) and scale values (200, 400, 600, 800 and 1000 in the drawing) are displayed with a large size at a front side and are displayed with a small size at an inner part, thereby obtaining the same effect. In addition, the process of changing the thickness of the coordinate axis, the scale interval and the size of the character may be performed by applying the above-described shade process.

(3-4) Moving Image

As described above, the display of the 3D stereoscopic image on the output unit 142 (display 43) may be arbitrarily rotated, enlarged or reduced based on the user input signal from the input unit 141 (mouse 41, keyboard 42, or the like). When rotating the 3D stereoscopic image, as shown in FIG. 3, a coordinate axis is preferably displayed at each side of a stereoscopic shape (cube) configuring a coordinate space 6. Since the stereoscopic shape of the coordinate space 6 is clarified by such a coordinate axis, it is easy to recognize a change in direction of the three-dimensional distribution map when the 3D stereoscopic image is rotated.

The 3D stereoscopic image displayed on the display 43 may be optionally rotated by user input or may be continuously rotated in a constant direction slowly. By displaying the 3D stereoscopic image by a moving image which is continuously rotated, it is possible to increase a 3D effect as compared to the display of a still image.

Figure 9:
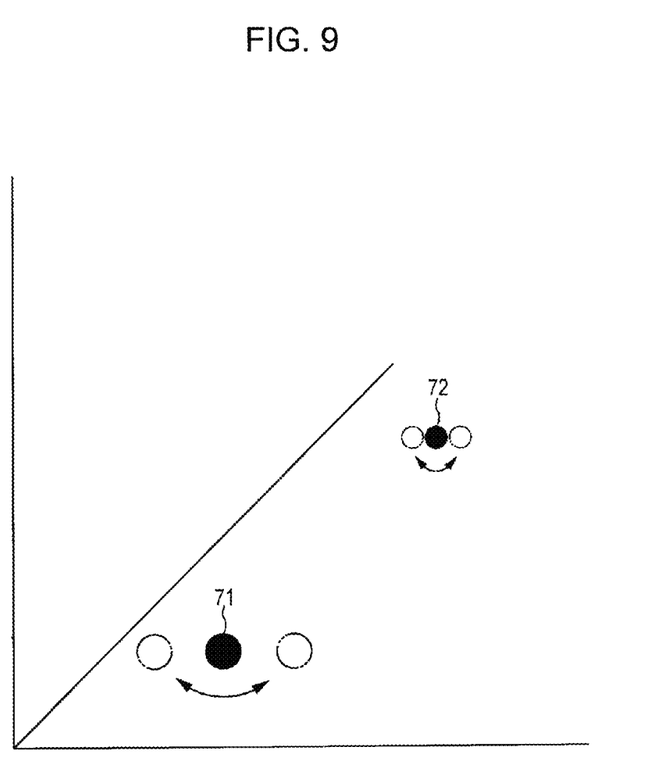
FIG. 9 is a conceptual diagram illustrating a stereoscopic observation image of a moving image in which a figure corresponding to a microparticle fluctuates.

In addition, the 3D stereoscopic image displayed on the display 43 may be displayed by a moving image in which the figure corresponding to the microparticle fluctuates. At this time, the figure observed at the front side largely fluctuates as compared to the figure observed at the inner part at the time of stereoscopic viewing. A conceptual diagram of a stereoscopic image of the figure to which a fluctuation operation is applied is shown in FIG. 9. The reference numerals 71 and 72 fluctuate from side to side as denoted by an arrow of the drawing, a fluctuation width from side to side is large in the reference numeral 71 observed at the front side and is small in the reference numeral 72 observed at the inner part. By the display of the figure observed at the front side which largely fluctuates as compared to the figure observed at the inner part at the time of stereoscopic viewing, it is possible to give a depth to the stereoscopic image of the 3D stereoscopic image and improve a 3D effect.

As described above, the 3D data analysis apparatus according to the present disclosure has been to studied to improve the 3D effect of the displayed 3D stereoscopic image. Accordingly, even in a three-dimensional distribution map formed of points (figures corresponding to microparticles) and lines (coordinate axes), the user may perform analysis of measurement data while properly viewing the stereoscopic image and easily and intuitively specify microparticles and microparticle sub-groups to be analyzed on the distribution map.

4. 3D Data Analysis Program

A 3D data analysis program according to the present disclosure calculates a position in the coordinate space using three independent variables selected from measurement data of microparticles as coordinate axes, calculates a figure from another independent variable selected from the measurement data of the microparticles, and executes a step of creating a 3D stereoscopic image showing a characteristic distribution of the microparticles and a step of displaying the 3D stereoscopic image on a computer.

When the above-described embodiments are described with reference to FIGS. 1 and 2 again, the 3D data analysis program is stored in the hard disk 30 (see reference numeral 31 of the drawing). The 3D data analysis program is read from the memory 20 under the control of the CPU 10 and the operating system (OS) 43 so as to execute a process of creating the 3D stereoscopic image of the three-dimensional distribution flow in the data processing unit 120 and a process of displaying the 3D stereoscopic image on the display unit 142.

The 3D data analysis program may be recorded on a computer-readable recording medium. Although the recording medium is not specially limited if a computer-readable recording medium, for example, a disk-shaped recording medium such as a flexible disk or a CD-ROM is used. In addition, a tape type recording medium such as a magnetic tape may be used.

It should be understood by those skilled in the art that various modifications, combinations, sub-combinations and alterations may occur depending on design requirements and other factors insofar as they are within the scope of the appended claims or the equivalents thereof.

The invention is claimed as follows:

1. A data analysis apparatus comprising:
a data storage unit configured to store measurement data of microparticles;
an input unit configured to select at least four independent variables based on the measurement data;
a data processing unit configured to:
calculate a position of at least one of the microparticles in a three-dimensional (3D) coordinate space using three variables of the selected at least four independent variables as coordinate axes,
plotting the at least one of the microparticles using the three variables at the calculated position in the 3D coordinate space,
calculate a figure for the at least one of the microparticles at the position based on a remaining variable of the selected at least four independent variables, and
create a 3D stereoscopic image showing a characteristic distribution of the microparticles using the position and the figure; and
a display unit configured to display the 3D stereoscopic image, wherein in the 3D stereoscopic image, a coordinate axis lying along a direction of observation of the coordinate axes is displayed to have varying thickness.

2. The data analysis apparatus according to claim 1, wherein the data processing unit calculates the shape, size and/or color of the figure from the measurement data of the remaining variable.

3. The data analysis apparatus according to claim 1, wherein the data processing unit calculates the position from the measurement data of a variable of the three variables showing optical characteristics of the microparticles and calculates the figure from the measurement data of another variable of the selected at least four independent variables showing electrical characteristics.

4. The data analysis apparatus according to claim 1, wherein the data processing unit calculates the position from measurement data of intensity of scattered light and/or fluorescence generated from the microparticles to which light is irradiated and calculates a size of the figure from measurement data of impedance of the microparticles.

5. The data analysis apparatus according to claim 1, wherein the 3D stereoscopic image is rotated, enlarged and reduced and is displayed on the display unit based on an input signal from the input unit.

6. The data analysis apparatus according to claim 1, wherein a shape of the figure is a polyhedron formed of a combination of polygons having a predetermined shape.

7. The data analysis apparatus according to claim 1, wherein, in the display of the 3D stereoscopic image, shading of the figure observed from a front part along the direction of observation is darker than the shading of the figure observed at an inner part along the direction of observation of the 3D stereoscopic image.

8. The data analysis apparatus according to claim 1, wherein, in the 3D stereoscopic image, the coordinate axes are displayed on sides of a stereoscopic shape configuring the coordinate space.

9. The data analysis apparatus according to claim 1, wherein a front part of the coordinate axis lying along the direction of observation is displayed to be thicker than an inner part of the coordinate axis lying along the direction of observation.

10. The data analysis apparatus according to claim 1, wherein the 3D stereoscopic image is displayed by a moving image in which the figure fluctuates and the figure observed from a front part along the direction of observation is displayed to fluctuate largely as compared to the figure observed at an inner part along the direction of observation when observing a stereoscopic image of the moving image.

11. The data analysis apparatus according to claim 1, wherein the display unit is a display, and glasses for stereoscopically viewing the 3D stereoscopic image displayed on the display are included.

12. The data analysis apparatus according to claim 1, wherein the measurement data of the microparticles is obtained from a flow cytometer.

13. The data analysis apparatus according to claim 1, wherein the 3D stereoscopic image displayed on the display unit is configured to be continuously rotated in a predetermined direction.

14. The data analysis apparatus according to claim 1, wherein the 3D stereoscopic image displayed on the display unit is rotated based on an input signal from the input unit.

15. A microparticle analysis system comprising the data analysis apparatus according to claim 1 and a microparticle measurement apparatus, wherein the data analysis apparatus and the microparticle measurement apparatus are connected to each other.

16. A data analysis method comprising:
selecting at least four independent variables based on measurement data of microparticles;
calculating a position of at least one of the microparticles in a three-dimensional (3D) coordinate space using three variables of the selected at least four independent variables as coordinate axes;
plotting the at least one of the microparticles using the three variables at the calculated position in the 3D coordinate space;

calculating a figure for the at least one of the microparticles at the position based on a remaining variable of the selected at least four independent variables;

creating a 3D stereoscopic image showing a characteristic distribution of the microparticles using the position and the figure; and displaying the 3D stereoscopic image, wherein in the 3D stereoscopic image, a coordinate axis lying along a direction of observation of the coordinate axes is displayed to have varying thickness.

17. A non-transitory computer readable medium, having stored thereon, computer executable instructions that causes a computer to perform the steps comprising:

calculating a position of one or more microparticles in a three-dimensional (3D) coordinate space using three variables selected independently from measurement data of the one or more microparticles as coordinate axes;

plotting at least one of the one or more microparticles using the three variables at the calculated position in the 3D coordinate space;

calculating a figure for the one or more microparticles based on another independent variable selected from the measurement data of the one or more microparticles;

creating a 3D stereoscopic image showing a characteristic distribution of the one or more microparticles using the position and the figure; and displaying the 3D stereoscopic image, wherein in the 3D stereoscopic image, a coordinate axis lying along a direction of observation of the coordinate axes is displayed to have varying thickness.

* * * * *